US012740751B2

(12) United States Patent
Stewart et al.

(10) Patent No.: US 12,740,751 B2
(45) Date of Patent: Sep. 22, 2026

(54) DEVICE FOR MEASURING PERIODIC VITAL SIGNALS EMITTED BY AN INDIVIDUAL, ASSOCIATED WITH A SAFETY APPARATUS OF A VEHICLE

(71) Applicant: Wormsensing, Grenoble Cedex (FR)

(72) Inventors: Paul Stewart, Le Bouscat (FR); Catherine Cadieux, Grenoble (FR); Thomas Lorne, Eguilles (FR)

(73) Assignee: WORMSENSING, Seyssinet-Pariset (FR)

( * ) Notice: Subject to any disclaimer, the term of this patent is extended or adjusted under 35 U.S.C. 154(b) by 202 days.

(21) Appl. No.: 18/561,471

(22) PCT Filed: May 11, 2022

(86) PCT No.: PCT/FR2022/050904

§ 371 (c)(1),
(2) Date: Nov. 16, 2023

(87) PCT Pub. No.: WO2022/243625

PCT Pub. Date: Nov. 24, 2022

(65) Prior Publication Data

US 2024/0130685 A1 Apr. 25, 2024
US 2024/0225551 A9 Jul. 11, 2024

(30) Foreign Application Priority Data

May 18, 2021 (FR) ........................................ 2105201
Jun. 23, 2021 (FR) ........................................ 2106682

(51) Int. Cl.
*A61B 5/00* (2006.01)
*A61B 5/0205* (2006.01)
(Continued)

(52) U.S. Cl.
CPC .......... *A61B 5/6893* (2013.01); *A61B 5/0205* (2013.01); *A61B 5/1102* (2013.01); *A61B 5/113* (2013.01); *A61B 2562/18* (2013.01)

(58) Field of Classification Search
CPC ... A61B 5/6893; A61B 5/0205; A61B 5/1102; A61B 5/113; A61B 2562/18
(Continued)

(56) References Cited

U.S. PATENT DOCUMENTS 5,853,005 A 12/1998 Scanlon
10,575,087 B2 2/2020 Miyoshi et al.
(Continued)

FOREIGN PATENT DOCUMENTS

CN 106500826 A 3/2017
CN 106725395 A 5/2017
(Continued)

OTHER PUBLICATIONS

Decision to Grant a Patent received for Japanese Patent Application No. 2023-571490, mailed on Feb. 24, 2026, 5 pages (2 pages of English Translation and 3 pages of Original Document).
(Continued)

*Primary Examiner* — Jack K Wang
(74) *Attorney, Agent, or Firm* — TraskBritt

(57) ABSTRACT

A device for measuring at least one periodic vital signal from an individual, intended to be attached to a safety apparatus of a vehicle so as to be arranged between the individual and the apparatus, the device comprising: a vibration sensor comprising: a stack of layers and including an active layer made of piezoelectric material and two contact electrodes arranged on at least one face of the active layer, a flexible support layer including a printed circuit comprising two electrical terminals, the support layer being intended to be arranged on the individual, an electrical connection layer,
(Continued)

arranged between the stack of layers and the support layer, for connecting each contact electrode to an electrical terminal, an acoustic attenuation member intended to be arranged between the safety apparatus and the vibration sensor, the member being integral with the support layer and arranged above and spaced apart from the stack of layers.

19 Claims, 6 Drawing Sheets

(51) Int. Cl.
*A61B 5/113* (2006.01)
*A61B 5/11* (2006.01)

(58) Field of Classification Search
USPC ........................................................ 340/573.1
See application file for complete search history.

(56) References Cited

U.S. PATENT DOCUMENTS

| | | | | |
|---|---|---|---|---|
| 2006/0155175 | A1* | 7/2006 | Ogino | A61B 5/02438 600/595 |
| 2007/0205701 | A1 | 9/2007 | Grumm | |
| 2010/0087748 | A1* | 4/2010 | Tobola | A61B 5/113 600/529 |
| 2011/0224875 | A1* | 9/2011 | Cuddihy | B60K 28/06 701/1 |
| 2012/0259181 | A1* | 10/2012 | Fujita | A61B 5/4035 600/300 |
| 2013/0033382 | A1* | 2/2013 | Fung | A61B 5/6893 340/573.1 |
| 2014/0276090 | A1* | 9/2014 | Breed | A61B 5/1455 600/473 |
| 2015/0119758 | A1 | 4/2015 | Rogers et al. | |
| 2018/0020931 | A1 | 1/2018 | Shusterman | |
| 2018/0307927 | A1* | 10/2018 | Hutchinson | G06V 20/46 |
| 2019/0239598 | A1* | 8/2019 | Ver Hoven | A44B 11/2561 |
| 2019/0325185 | A1 | 10/2019 | Tang | |
| 2019/0357834 | A1* | 11/2019 | Aarts | A61B 5/7246 |
| 2020/0405998 | A1 | 12/2020 | Franceschetti et al. | |
| 2021/0319198 | A1 | 10/2021 | Seomoon et al. | |
| 2022/0354428 | A1 | 11/2022 | Han et al. | |
| 2023/0380794 | A1 | 11/2023 | Sasaki | |
| 2024/0225551 | A9 | 7/2024 | Stewart et al. | |

FOREIGN PATENT DOCUMENTS

| | | | |
|---|---|---|---|
| CN | 112716475 | A | 4/2021 |
| EP | 3144074 | A1 | 3/2017 |
| JP | 2005-095408 | A | 4/2005 |
| JP | 2012-221868 | A | 4/2014 |
| JP | 2014-525800 | A | 10/2014 |
| JP | 2015-521062 | A | 7/2015 |
| JP | 2015-186910 | A | 10/2015 |
| JP | 2019-010497 | A | 1/2019 |
| JP | 2019-117200 | A | 7/2019 |
| KR | 10-1957110 | B1 | 3/2019 |
| WO | 2015/064216 | A1 | 5/2015 |
| WO | 2015/093356 | A1 | 6/2015 |
| WO | 2016/026028 | A1 | 2/2016 |
| WO | 2019/163740 | A1 | 8/2019 |

OTHER PUBLICATIONS

Fu et al., Chinese Patent Document CN-112716475-A, citing to translation from Clarivate Analytics (Year: 2021).
Japanese Notice of Reasons for Refusal for Application No. 2023-571491 dated Mar. 2, 2026, 12 pages with machine translation.
Kanegae et al., WIPO Publication WO 2019/163740 A1—citing to translation from Clarivate Analytics (Year: 2019).
MEMSnet, "Material: Lead Zirconate Titanate (PZT)", MNX | MEMS & Nanotechnology Exchange, accessed on Feb. 7, 2026, accessed at https://www.memsnet.org/material/leadzirconatetitanatepzt/ (Year: 2026).
Sabet et al., "Analytical and Computational Solutions to Piezoelectric Bending: A Comparative Study", NSTI—Nanotech, vol. 3, 2007 (Year: 2007).
Delobelle et al., True Yong Modulus of Pb(Zr,Ti)O3 Films Measured by Nanoindentation, Applied Physics Letters, vol. 85, No. 22, (Nov. 29, 2004), 4 pages.
International Search Report for Application No. PCT/FR2022/050904 dated Aug. 17, 2022, 3 pages.
International Written Opinion for Application No. PCT/FR2022/050904 dated Aug. 17, 2022, 7 pages.
Tsuchiya et al., Fabrication of Smart Material PZT Thin Films by RF Magnetron Sputtering Method in Micro Actuators, JSME International Journal, Series A, vol. 49, No. 2, (2006), pp. 201-208.

* cited by examiner

DEVICE FOR MEASURING PERIODIC VITAL SIGNALS EMITTED BY AN INDIVIDUAL, ASSOCIATED WITH A SAFETY APPARATUS OF A VEHICLE

CROSS-REFERENCE TO RELATED APPLICATIONS

This application is a national phase entry under 35 U.S.C. § 371 of International Patent Application PCT/FR2022/050904, filed May 11, 2022, designating the United States of America and published as International Patent Publication WO 2022/243625 Al on Nov. 24, 2022, which claims the benefit under Article 8 of the Patent Cooperation Treaty of French Patent Application Serial No. FR2105201, filed May 18, 2021 and of French Patent Application Serial No. FR2106682, filed Jun. 23, 2021.

TECHNICAL FIELD

The present disclosure relates to the field of collecting periodic vital signals emitted by the human body, in particular, heart beats or respiratory rate. It relates to, in particular, a device provided with a vibration sensor, which device is associated with a safety apparatus (for example, the seatbelt) of a vehicle and allows the measurement of the heart beats of the user.

BACKGROUND

Road accidents are a major problem for developed countries. The main causes of accidents include fatigue and falling asleep at the wheel. Within the European Union (EU), it is evaluated that the latter causes are responsible for 20% to 35% of serious accidents and close to 6,000 deaths per year. The EU believes that integrating on-board fatigue detectors in vehicles would make it possible to save 4,000 lives and prevent tens of thousands of injuries each year.

In parallel to this, there has been an acceleration of the research and development around the topic of autonomous vehicles. If, in actual fact, autonomous driving is still far from being operational for market release, everything appears to indicate that a first step of "partial autonomous driving" under the responsibility of a driver will become common in the coming years. In this context, it will therefore be necessary to ensure that the driver has all of his or her vigilance and reaction capacities, should they have to resume control in an emergency situation. It is in this regard that several public and private entities, including motor vehicle and equipment manufacturers, are currently attempting to find viable solutions for automatic fatigue detection in vehicles.

Some envisaged solutions, such as connected watches, bracelets or garment belts, are too invasive for the user and ensure monitoring of the physiological variables of the driver only if the latter thinks to wear them and/or to connect them.

Other solutions propose integrating a module for measuring the heart rate on the seatbelt of the vehicle, at the driver's torso. For example, document CN106725395 proposes a module for measuring the heart rate that comprises two metal electrodes sandwiching the polyester strap of the seatbelt. The heart beats force an insulating material arranged between the two metal electrodes to contract: the distance between the two metal electrodes changes, thus modifying the capacitance value and providing information on the heart rate of the driver.

BRIEF SUMMARY

The present disclosure also relates to a solution associated with a vehicle safety apparatus. It relates to, in particular, a compact and sensitive device, provided with a vibration sensor, able to capture and analyze periodic vital signals of an individual in their vehicle.

The present disclosure relates to a device for measuring at least one periodic vital signal from an individual, intended to be attached to a safety apparatus of a vehicle so as to be arranged between the individual and the apparatus. The device comprises a vibration sensor comprising:

- a stack of layers extending parallel to a main plane and including an active layer made of piezoelectric material and two contact electrodes arranged on at least one face of the active layer,
- a flexible support layer configured to transmit a deformation to the active layer of the stack of layers at each pulse of the vital signal, the support layer extending parallel to the main plane and including a printed circuit comprising two electrical terminals, the support layer being intended to be arranged against the individual,
- an electrical connection layer, arranged between the stack of layers and the support layer, for connecting each contact electrode to an electrical terminal.

The device further comprises an acoustic attenuation member, intended to be arranged between the safety apparatus and the vibration sensor, the member being rigidly connected to the support layer and arranged above and spaced apart from the stack of layers.

According to other advantageous non-limiting features of the present disclosure, taken alone or according to any technically feasible combination:

- the acoustic attenuation member comprises a cover, composed of a flexible material having a hardness of between 10 Shore 00 and 80 Shore 00, and rigidly connected to the support layer by its periphery;
- the cover is heterogeneous and comprises a second rigid material chosen from metals or polymers having a hardness of between 10 Shore D and 80 Shore D;
- the device comprises a mechanical attenuation member, on or integrated in whole or in part in the acoustic attenuation member, the mechanical attenuation member being intended to be in direct or indirect contact with the safety apparatus;
- the mechanical attenuation member comprises at least one damper and optionally a body forming a mass;
- the active layer of the stack of layers has a thickness of less than or equal to 20 microns and a Young's modulus greater than or equal to 60 GPa;
- the device comprises an impedance matching layer (40), having an acoustic impedance between $5\cdot10^5$ Pa*s/m and $3\cdot10^6$ Pa*s/m, and arranged on a face of the support layer opposite the one in contact with the electrical connection layer;
- the piezoelectric material of the active layer is chosen from ceramics in monocrystalline, poly-crystalline or composite form;
- the contact electrodes have a cumulative thickness of less than twice the thickness of the active layer;
- the support layer is self-supporting and has a thickness of less than or equal to 500 microns;

- the impedance matching layer has a thickness greater than or equal to 10 microns;
- the electrical connection layer is formed by an interposer or by an anisotropic conductive film;
- the support layer includes a membrane disposed on a face of the printed circuit opposite the one in contact with the electrical connection layer;
- the stack of layers and the support layer, respectively, have a first surface area and a second area, in the main plane, the first surface area being less than or equal to 30% of the second surface;
- the support layer comprises a stiffening structure, rigidly connected to a peripheral zone of the support layer, the sound attenuation member in turn being rigidly connected to the stiffening structure;
- the printed circuit comprises a wire connection element, for connecting the vibration sensor to an electronic terminal;
- the vibration sensor comprises a peripheral seal;
- the device further comprises an electronic terminal connected to the vibration sensor, to analyze and interpret the raw signal and extract the periodic vital signal or an output parameter representative of the periodic vital signal;
- the electronic terminal comprises an analog stage for conditioning the raw signal measured by the vibration sensor, an analog to digital conversion stage of the signal coming from the conditioning stage, a digital signal processing stage, for shaping the digital signal and calculating an output parameter representative of the vital signal;
- the electronic terminal comprises a communication stage with an external system.

The present disclosure also relates to a safety system of a vehicle, comprising:

- a safety apparatus, associated with a seat and rigidly connected to a chassis of the vehicle at least at one direct or indirect contact point,
- a device for measuring at least one periodic vital signal of an individual, as above, attached to the safety apparatus by a sliding fastener, and
- at least one mechanical energy absorber placed at least at one contact point, so as to insulate the safety apparatus from the mechanical vibrations of the chassis.

The safety apparatus can be directly connected to the chassis by at least three contact points, and a mechanical energy absorber is then integrated into at least one of the contact points.

The safety apparatus can be connected to the seat, which is rigidly connected to the chassis by at least one contact point, and a mechanical energy absorber is then integrated into the contact point.

BRIEF DESCRIPTION OF THE DRAWINGS

Other features and advantages of the present disclosure will emerge from the following detailed description of embodiments of the present disclosure with reference to the appended figures.

The same references in the figures may be used for elements of the same type. Some figures contain schematic depictions that, for the sake of readability, are not to scale: In particular, the thicknesses of the layers along the z axis are not to scale with respect to the lateral dimensions along the x and y axes; and the relative thicknesses of the layers between them are not necessarily respected.

The different possibilities (variants and embodiments depicted and/or detailed in the description to follow) must be understood as not being exclusive of one another and may be combined together.

DETAILED DESCRIPTION

Figure 1:
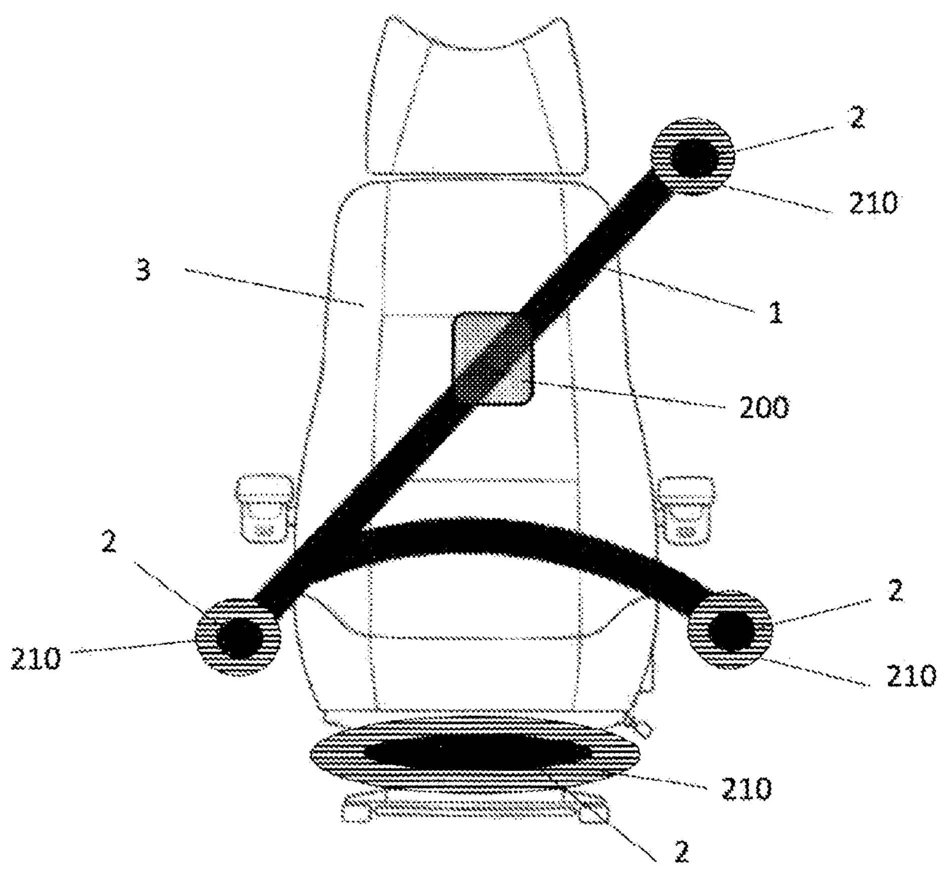
FIG. 1 shows a safety system comprising a device for measuring at least one periodic vital signal of an individual in a vehicle, in accordance with the present disclosure.

The present disclosure relates to a device 200 for measuring at least one periodic, regular or irregular vital signal of an individual. The periodic vital signal may be, in particular, the heart rate or the respiratory rate. The device 200 is intended to be attached to a safety apparatus 1, in a vehicle, so that the device 200 is arranged between the individual and the apparatus 1 (FIG. 1). The term "safety apparatus 1" is understood to mean any apparatus intended to secure the user on a seat 3 of the vehicle, in particular, a seatbelt, one or more safety bar(s), a safety harness, etc. The vehicle can also be understood broadly, and includes any mode of transportation for people, rolling, flying, gliding or floating.

The device 200 is preferentially attached to the safety apparatus 1 by a sliding fastener, that is, a fastener that is able to clip onto the apparatus 1 in order to immobilize the device 200 in a given position, and able to slide (when it is unclipped), to allow each user to adjust the position of the device 200 on their thorax, according to their size and their corpulence. Optionally, the fastening system may allow latitude of movement around the operating position for user comfort.

The device 200 comprises a vibration sensor 100 and an acoustic attenuation member 110.

Various configurations of vibration sensors 100, according to the present disclosure, are shown in FIGS. 2A, 2B, 3A and 3B and will now be described.

The vibration sensor 100 comprises a stack of layers 10 extending parallel to a main plane (x, y), that is to say that the main faces of this stack 10 are substantially parallel to the main plane (x, y) and that the thickness of the stack 10 is measured along an axis z normal to the main plane. The term "layer," in the present disclosure, implies that the thickness of the layer (or of the stack of layers) is generally significantly less than the lateral dimensions (in the main plane) of the layer.

The stack of layers 10 includes an active layer 11 made from piezoelectric material, preferentially chosen from piezoelectric ceramics, in a monocrystalline, poly-crystalline or composite form (corresponding to a dispersion of piezoelectric ceramic powder in a matrix, generally polymer). As an example, mention may be made of the following ceramics: lithium niobate (LiNbOs), lithium tantalate (LiTaOs), potassium niobate (KNbOs), (BaTiOs), quartz (SiO2), lead magnesium niobate-lead titanate (PMN-PT), lead zirconate titanate (PZT), materials based on potassium sodium niobium lithium antimony (KNN-LS) or modified with calcium titanate (KNN-LS-CT), materials based on potassium sodium lithium niobium tantalum antimony (KNNLNTS), bismuth sodium titanate (BNKLBT), etc.

As is known per se, the active layer 11 made of piezoelectric material will polarize (and therefore generate a flow of charges leading to a measurable electrical signal) if it undergoes a deformation, in particular here, deformation caused by the angular frequency of the periodic vital signal.

The active layer 11 advantageously has a thickness less than or equal to 20 microns and a Young's modulus greater than or equal to 60 GPa. These physical characteristics confer a high level of sensitivity on the active layer 11 (linked to its small thickness and to the fact that the measured voltage is all the greater, for a given deformation, when the Young's modulus is high), and a high signal-to-noise ratio on the sensor 100 for the detection of acoustic waves in the frequencies relating to the targeted periodic vital signals. The low thickness of the active layer 11 also promotes the compactness of the sensor 100.

The thickness of the active layer 11 can be less than or equal to 10 microns, or even less than or equal to 5 microns, to further improve the detection sensitivity of the acoustic waves. It will be ensured that an active layer 11 thickness is sufficient to generate bias voltages typically greater than 500 microvolts during a deformation.

The lateral dimensions (in the main plane (x, y)) of the active layer 11 may be chosen, for example, to be between 500 microns and 50 mm, small dimensions being of course preferred for reasons of compactness of the vibration sensor 100.

The stack of layers 10 also includes two contact electrodes 12, 13, arranged on one of the faces of the active layer 11 or on both faces (namely on either side of the active layer 11), to allow free circulation of the charges, set in motion by the polarization (representative of the periodic vital signal) of the layer 11.

Preferably, the contact electrodes 12, 13 have a cumulative thickness less than twice the thickness of the active layer 11, or even less than the thickness of the active layer 11; each electrode 12, 13 therefore advantageously has a thickness of less than 10 microns, or even less than 5 microns.

The contact electrodes 12, 13 may be formed from pure metal materials (for example, Ag, Au, Pd, Pt, Cu, Ni, W or Ti), conductive alloys, or 2D conductive materials (for example, graphene). A diffusion barrier (for example, made of TiN, WN or TaN) and an adhesion layer (for example, made of Cr or Ti) may be provided between the conductive material of each electrode 12, 13 and the active layer 11.

Advantageously, the stack of layers 10 consists of the active layer 11 and of the two contact electrodes 12, 13 only.

The vibration sensor 100 also comprises a flexible support layer 30, extending parallel to the main plane (x, y) and including a printed circuit 31 comprising two electrical terminals 32, 33. An electrical connection layer 20 (which also forms part of the vibration sensor 100) is arranged between the stack of layers 10 and the support layer 30, to connect each contact electrode 12, 13 to an electrical terminal 32, 33.

The electrical connection layer 20 is formed by an interposer or by an anisotropic conductive film (ACF). In all cases, the objective is that the two contact electrodes 12, 13 of the stack of layers 10 can be reached at one and the same face of the stack 10; this face (called the lower face) being then associated with the connection layer 20. In the case where the contact electrodes 12, 13 are respectively arranged on the lower face and the other face (called upper face) of the active layer 11, it is advantageous to provide a conductive via 14 passing through the active layer 11 and electrically connecting the electrode 12, arranged on the upper face, to a stud **12*a* arranged on the lower face and electrically insulated from the other electrode 13** also arranged on the lower face.

An interposer may be composed of thermoplastic (insulating) resin and an electrically conductive material (for example, nickel) allowing the connection between each contact electrode 12, 13 and an electrical terminal 32, 33.

An anisotropic conductive film (ACF) is conventionally composed of conductive beads dispersed in an insulating polymer matrix; when pressure or thermocompression is applied to the stack of layers 10/ACF 20/support layer 30, vertical electrical conduction is established between electrodes **12*a*, 13 and terminals 32, 33** (usually in extra thickness) via the conductive beads, whereas the interlayer zones remain insulating.

There are also anisotropic conductive adhesives (ACA) that could be used to form the electrical connection layer 20. These adhesives are based on the same principle as the aforementioned anisotropic conductive film (ACF), with the exception that the polymer matrix is replaced by a liquid precursor capable of being thermally activated to form the final polymer (by polymerization); the final result remains similar to the ACF (conductive beads dispersed in an insulating matrix), but given the fact that the application takes place in the liquid phase, it is possible to drastically reduce the thickness of the electrical connection layer 20.

A more basic solution can also be envisaged, namely the implementation of a conductive paste to connect each electrode and stud of the lower face, to an associated terminal 32, 33, and an insulating filler material to electrically insulate the electrodes **12*a*, 13 from one another and the terminals 32, 33** from one another.

The electrical connection layer 20 is only in contact with one of the main faces of the stack of layers 10; the edges and the other main face of the stack of layers 10 are totally free, without mechanical contact with the connection layer 20.

The electrical connection layer 20 is therefore at least partially composed of an electrically conductive material and provides a direct vertical connection between electrodes and terminals, conversely to a connection, for example, by cables or wires optionally coated in an insulator. The absence of cables improves the sensitivity of the vibration sensor 100, avoiding the introduction of additional stiffness into the structure, linked to the associated cables and welds.

Preferably, the electrical connection layer 20 is therefore in direct, homogeneous contact against the entire main face of the stack of layers 10. On the side of its other face, the layer 20 is advantageously in direct, homogeneous contact against a face of the support layer 30.

The electrical connection layer 20 typically has a thickness less than 50 microns, in particular, a thickness of between 1 micron and 10 microns.

The support layer 30 is a self-supporting layer, which advantageously has a thickness less than or equal to 500 microns. This gives the support layer 30 the required flexibility.

According to one variant, the support layer 30 is essentially composed of the material forming the printed circuit 31: for example, a composite of epoxy resin reinforced with glass fibers.

Figure 2A:
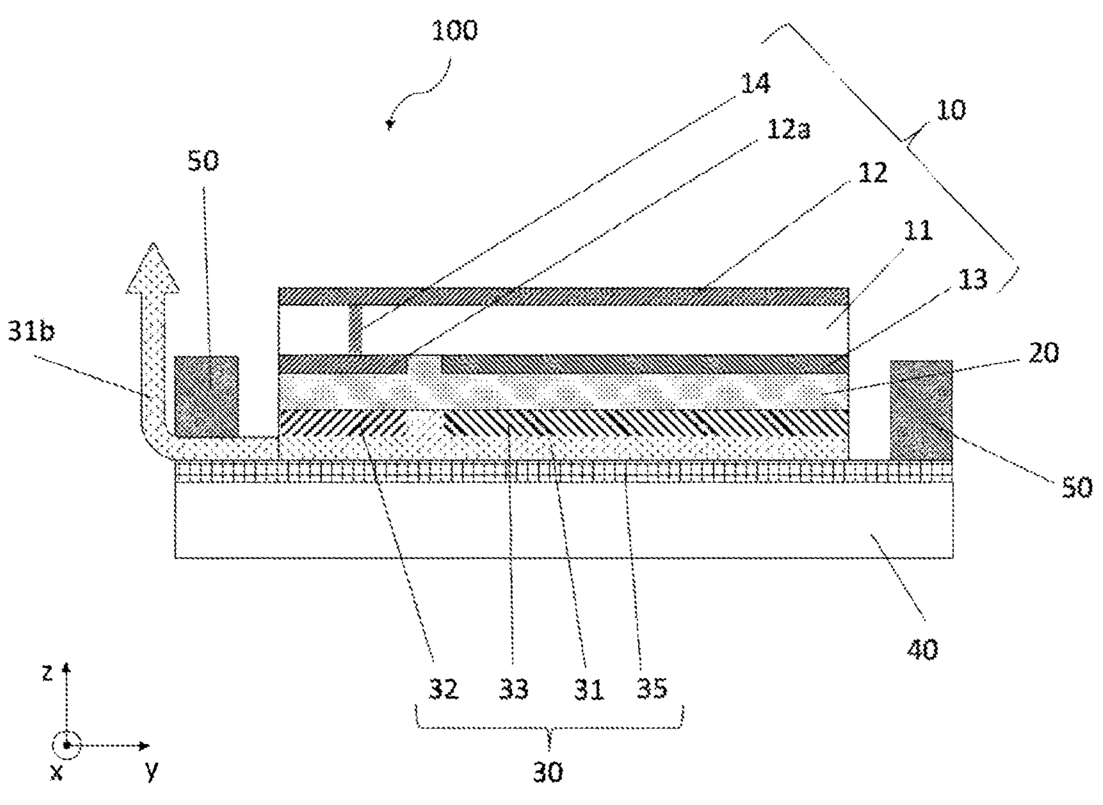
FIGS. 2A and 2B show all or part of a device according to the present disclosure, respectively, in cross-sectional schematic and perspective views.
Figure 3A:
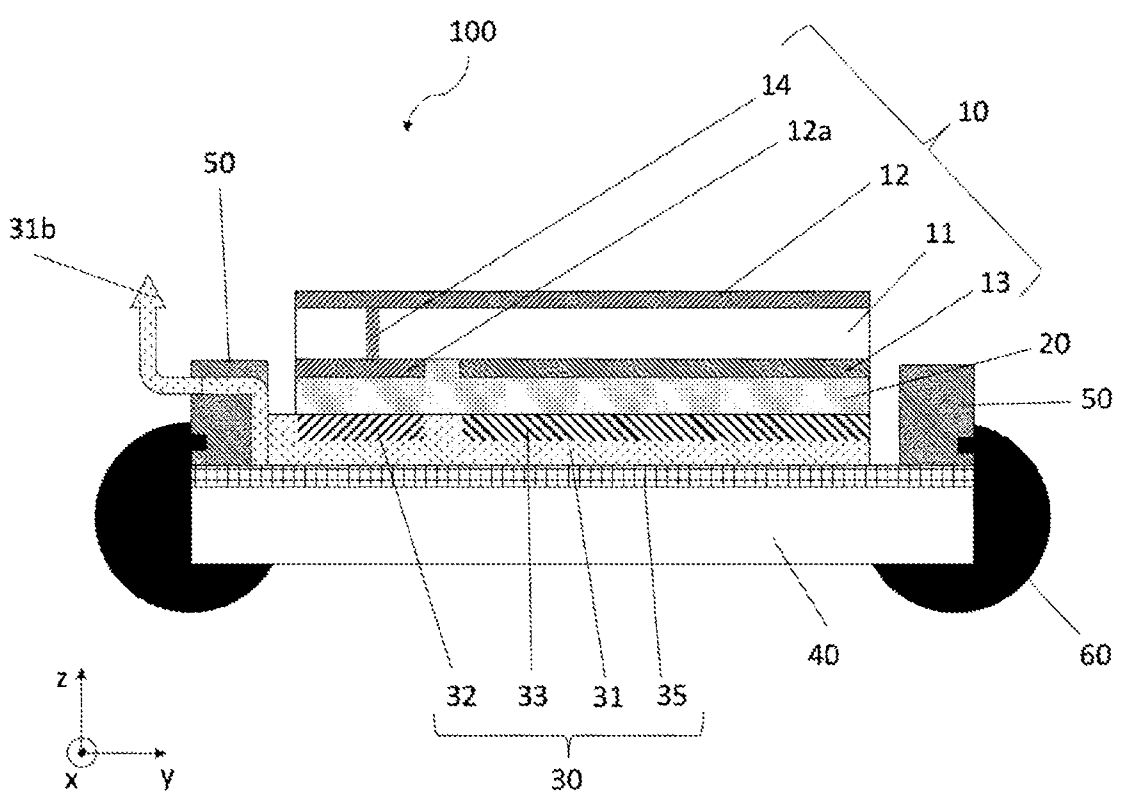
FIGS. 3A and 3B show all or part of a device according to the present disclosure, respectively, in cross-sectional schematic and perspective views.

According to another variant, the support layer 30 also comprises a membrane 35, the printed circuit 31 then being situated between the membrane 35 and the electrical connection layer 20 (FIGS. 2A and 3A). The material of the membrane 35, and its thickness, can thus be chosen and adjusted so as to impart the targeted flexibility to the support layer 30. The membrane 35 may be made of, for example, metal, polyvinyl chloride (PVC), or epoxy and glass fibers. By way of example, the membrane 35 (when it is present) may have a thickness of between 50 and 300 microns, and the printed circuit 31 may have a thickness of between 30 and 200 microns.

Typically, the support layer 30 has a stiffness of between 1150000 N/m and 6900000 N/m. The flexible nature of the support layer 30, linked to its thickness and its stiffness, makes it possible to effectively transmit a deformation to the active layer 11, at each pulse of the vital signal.

Advantageously, the stack of layers 10 and the support layer 30, respectively, have a first surface area and a second surface area, in the main plane (x, y), the first surface area being less than or equal to 30% of the second surface. The stack of layers 10 can be arranged in the central part of the support layer 30, in particular, for ease of assembly, or at the periphery to interfere as little as possible with the deformation of the support layer 30, which deformation is generated by the periodic pulsing of the vital signal that it is sought to measure, the overall objective is to optimize the deformation experienced by the stack of layers 10, as a function of the geometry of the vibration sensor 100. It should be noted that, although shown in a square form, the stack of layers 10 of the vibration sensor 100 may, of course, have any shape.

According to a first embodiment of the vibration sensor 100, the support layer 30 is intended to be in contact with the individual; the support layer 30 will then deform due to the periodic pulse of the vital signal, and transmit this deformation to the active layer 11 of the stack 10.

According to a second embodiment, the vibration sensor 100 further comprises an impedance matching layer 40, which has an acoustic impedance ideally between $5\cdot10^5$ Pa*s/m and $3\cdot10^6$ Pa*s/m. This acoustic impedance is knowingly chosen close to the acoustic impedance of the muscles and fat (impedance between $1.3\times10^6$ and $1.5\times10^6$ Pa*s/m), so as to promote the transmission of the pulses of the vital signal to the support layer 30. For example, the impedance matching layer 40 can be formed from silicone (acoustic impedance $1.6\times10^6$ Pa*s/m) or of bioplastic, for example, of brand ECOFLEX® (acoustic impedance $1.053\times10^6$ Pa*s/m).

The impedance matching layer 40 is arranged against the support layer 30, on a face of the support layer 30 opposite the one in contact with the electrical connection layer 20. The impedance matching layer 40 typically has a thickness greater than or equal to 10 microns, for example, between 50 microns and 5 mm. When the support layer 30 comprises a membrane 35, that membrane 35 is in contact with the impedance matching layer 40.

The impedance matching layer 40 is intended to be in contact with the individual. In addition to effectively transmitting the pulses due to its impedance matching with body tissues, this layer 40 also promotes the holding of the sensor 100 against the individual since its flexible and deformable material tends to "adhere" to the contact surface, by adhesion friction on the clothing. The presence of the impedance matching layer 40, in the second embodiment of the sensor 100, is therefore particularly favorable when the measurement environment is noisy around the individual whose vital signal is to be picked up.

Figure 3B:
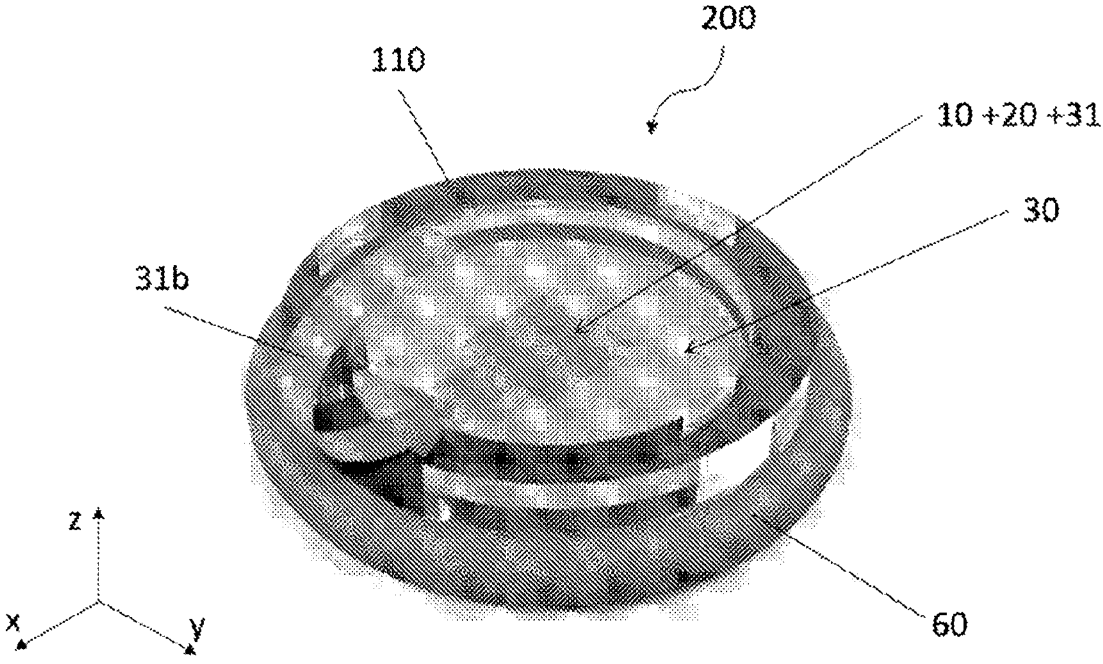

In either of the described embodiments, it may be advantageous for the vibration sensor 100 to comprise a peripheral seal 60 surrounding at least the impedance matching layer 40 (when present), as shown in FIGS. 3A and 3B, or surrounding all or part of the support layer 30 (in the absence of an impedance matching layer 40). This seal 60 makes it possible to accommodate the local topology when the sensor 100 is placed in contact with the individual.

Figure 2B:
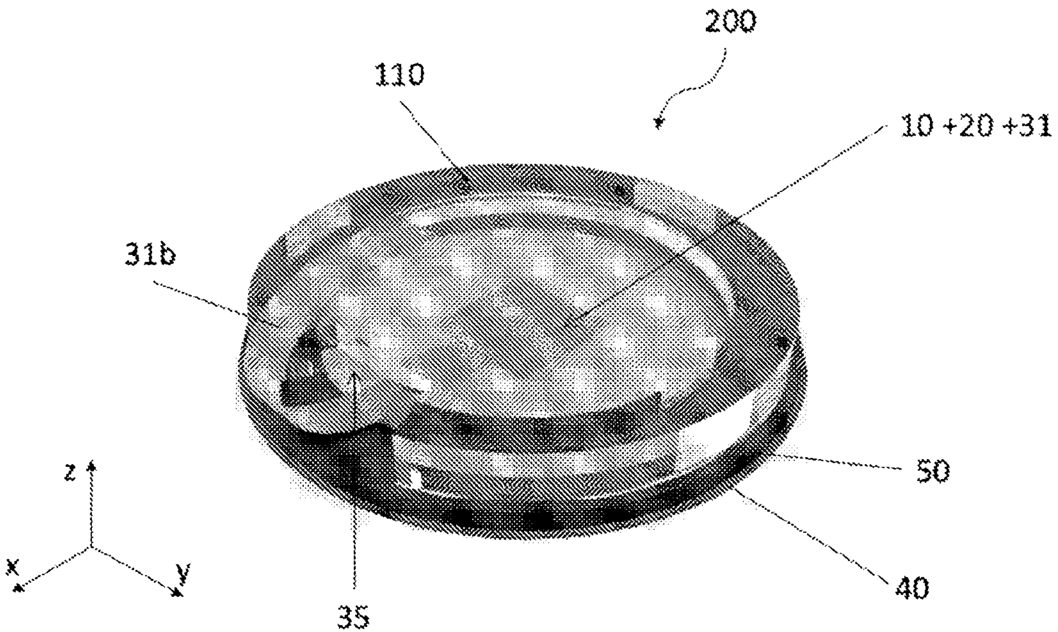
Figures 4A, 4B, 4C:
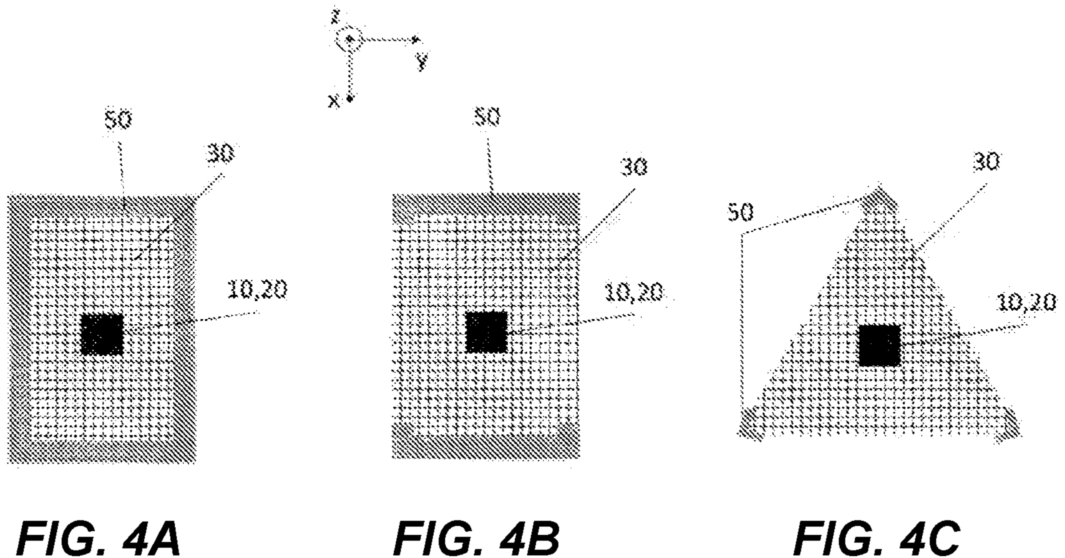
FIGS. 4A-4C show different shapes, in top view, of a vibration sensor for a device according to the present disclosure.

The support layer 30 of the vibration sensor 100 may also comprise a stiffening structure 50, rigidly connected to a peripheral zone of the support layer 30. The function of the stiffening structure 50 is to immobilize the periphery of the support layer 30 and of the impedance matching layer 40 (if present), and thus to accentuate their deformation generated by the periodic pulsing of the vital signal that it is sought to measure. The stiffening structure 50 may take various shapes such as, for example:

- a continuous frame (FIG. 4A), advantageously a ring (as shown in FIG. 2B), but optionally a rectangle, a triangle or another polygon; or
- a discontinuous frame, composed of two rigid areas (FIG. 4B), of three rigid areas (FIG. 4C), or even more.

The stiffening structure is advantageously formed from a material having a hardness greater than 30 Shore D, such as PET (polyethylene terephthalate), PMMA (polymethyl methacrylate), PU (polyurethane), PVC (polyvinyl chloride), PP (polypropylene), etc.

Given the reduced total thickness of the assembly comprising the stack of layers 10, the connection layer 20, the support layer 30 and potentially the impedance matching layer 40, it may be judicious to provide a system facilitating the handling of the sensor 100 and promoting its robustness: the stiffening structure 50 participates in such a system.

The device 200 according to the present disclosure comprises, in addition to the vibration sensor 100 that has just been described, an acoustic attenuation member 110, intended to be placed between the safety apparatus 1 and the vibration sensor 100.

This member 110 is arranged above and spaced apart from the stack of layers 10 of the vibration sensor 100, and it is rigidly connected to the support layer 30. Because it is located at a distance (along the z axis in the figures) from the stack of layers 10 (and thus without contact with the stack 10), typically at a distance of about 0.1 mm to 10 mm, it does not disturb the deformation thereof in connection with the support layer 30.

Figure 6A:
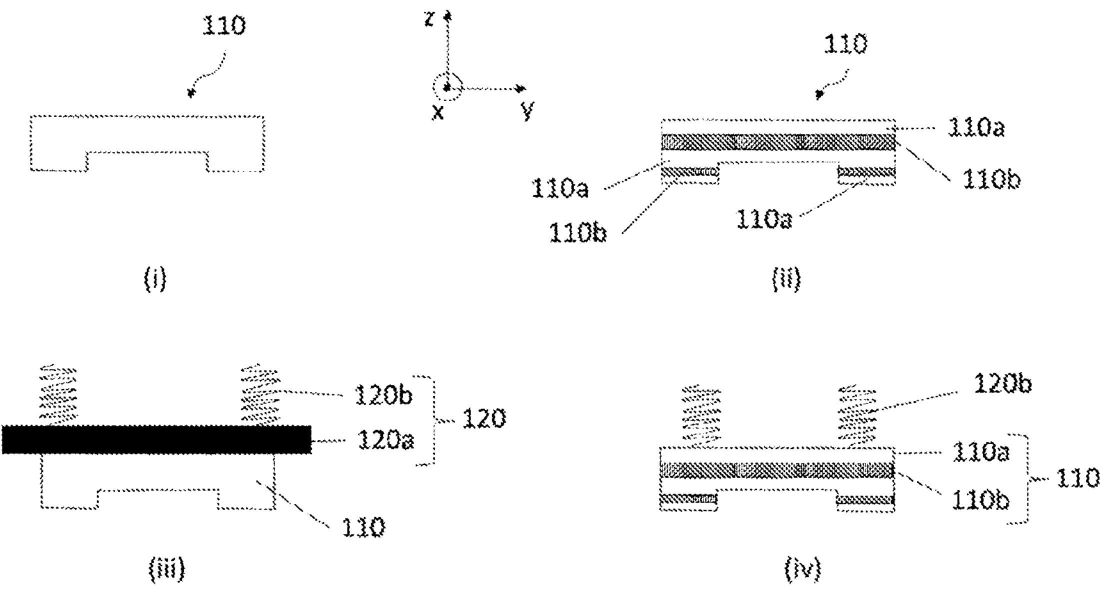
FIG. 6A shows two examples of acoustic attenuation member (i)(ii) and two examples of mechanical attenuation member (iii) (iv), for a device according to the present disclosure.

The acoustic attenuation member 110 advantageously takes the form of a cover (FIG. 6A (i),(ii)), the periphery of which is attached to the support layer 30, or when it is present, to the stiffening structure 50. By way of example, the thickness of the cover, above the stack of layers 10, can vary between 0.1 mm and 20 mm.

The acoustic attenuation member 110 aims to insulate the acoustic sensor 100 (and more particularly the support layer 30, which deforms with the vibrations, and the active layer 11, which is sensitive to the deformations) from the surrounding acoustic disturbances, which propagate in the air; namely, the sound of the engine, the sound of the road, the friction of air on the body, the voices of the passengers in the vehicle, the radio, etc. It is preferentially composed of a flexible material of the elastomer type such as silicone, sorbothane or rubber. More generally, the flexible material of the acoustic attenuation member 110 can be qualified by its Shore hardness: it has a hardness of between 10 Shore 00 and 80 Shore 00. In addition to its acoustic attenuation function, the member 110 participates in the robustness of the device 200 by protecting, in particular, the active layer 11 of the vibration sensor 100.

According to one variant, the acoustic attenuation member 110 may comprise several types of materials. If it is in the form of a cover, it is then referred to as a heterogeneous cover. The second material is chosen to be rigid, of a metal or polymer nature (for example, aluminum, or PVC). If the second material is a polymer, its hardness will preferentially be chosen between 10 Shore D and 80 Shore D.

The heterogeneous cover 110 is formed of an alternation of at least one first layer 110*a* of flexible material and at least one second layer 110*b* made of rigid material as shown in FIG. 6A (ii). The heterogeneous cover may also be composed of one or more porous material(s), such as, for example, a polyurethane foam.

Advantageously, the device 200 further comprises a mechanical attenuation member 120 whose role is to insulate the vibration sensor 100 from mechanical vibrations generated by the engine of the vehicle, by the road conditions and/or by the movements of the user, and transmitted to the safety apparatus 1 via the frame. The mechanical attenuation member 120 is therefore intended to be in contact (direct or indirect) with the safety apparatus 1. This mechanical attenuation member 120 can be arranged on the acoustic attenuation member 110 or wholly or partially integrated therein.

According to a first option, the mechanical attenuation member 120 is composed of a body 120*a* forming a mass and at least one damper 120*b* (FIG. 6A (iii)). The body 120*a* is arranged against the acoustic attenuation member 110 and the damper(s) is (are) placed on the side of the safety apparatus 1.

The damper 120*b* is defined by a stiffness k between 0 (friction alone) and 7 N/mm, and by a coefficient of friction f between 0 (stiffness alone) and 0.6. Each damper 120*b* may be formed, for example, by a metal spring, a resin, rubber or silicone pillar, or a simple, mixed (rubber/metal) or hydraulic damper element.

The body 120*a* has a mass m of between 1 g and 1 kg. The mechanical attenuation member 120 forms a "mass-spring-piston" system acting as a high-pass mechanical filter. By adjusting the mass m, the stiffness k and the coefficient of friction f, it is possible to change the properties of the mechanical filter and specifically to attenuate the mechanical vibrations transmitted to the safety apparatus 1.

It should be noted that the mass of the acoustic attenuation member 110 and that of the vibration sensor 100 must be taken into consideration, and added to the mass of the body 120*a* to arrive at the desired mechanical filter properties.

It is targeted for the mechanical filter to intersect/attenuate the parasitic frequencies located in the area of interest.

Thus, in the ideal case, it is desired for the cut-off frequency $$\left(F_c \propto \sqrt{\frac{k}{m}}\right)$$

of the filter to be around 150 Hz to cut all stray frequencies originating from the chassis (mechanical vibrations), and for its damping rate $$\left(\tau \propto \frac{f}{\sqrt{km}}\right)$$

to be closest to 1 to have the best possible attenuation. In practice, there are of course compromises to be made between this ideal case and the design constraints of the device 200.

According to a second option, the mechanical attenuation member 120 is partially integrated into the acoustic attenuation member 110, that is, the body 120*a* consists of a layer of rigid material 110*b* that makes up the acoustic attenuation member 110 (for example, in the form of a heterogeneous cover, as shown in FIG. 6A (iv)). The damping part 120*b* of the mechanical attenuation member 120 is then attached to the acoustic attenuation member 110 and can be formed by the different elements set out in the first option.

According to a third option, the mechanical attenuation member 120 is completely integrated into the acoustic attenuation member 110. For this, the mechanical attenuation member 120 (included in the acoustic attenuation member 110) can be formed from composite materials having viscoelastic properties.

Figure 6B:
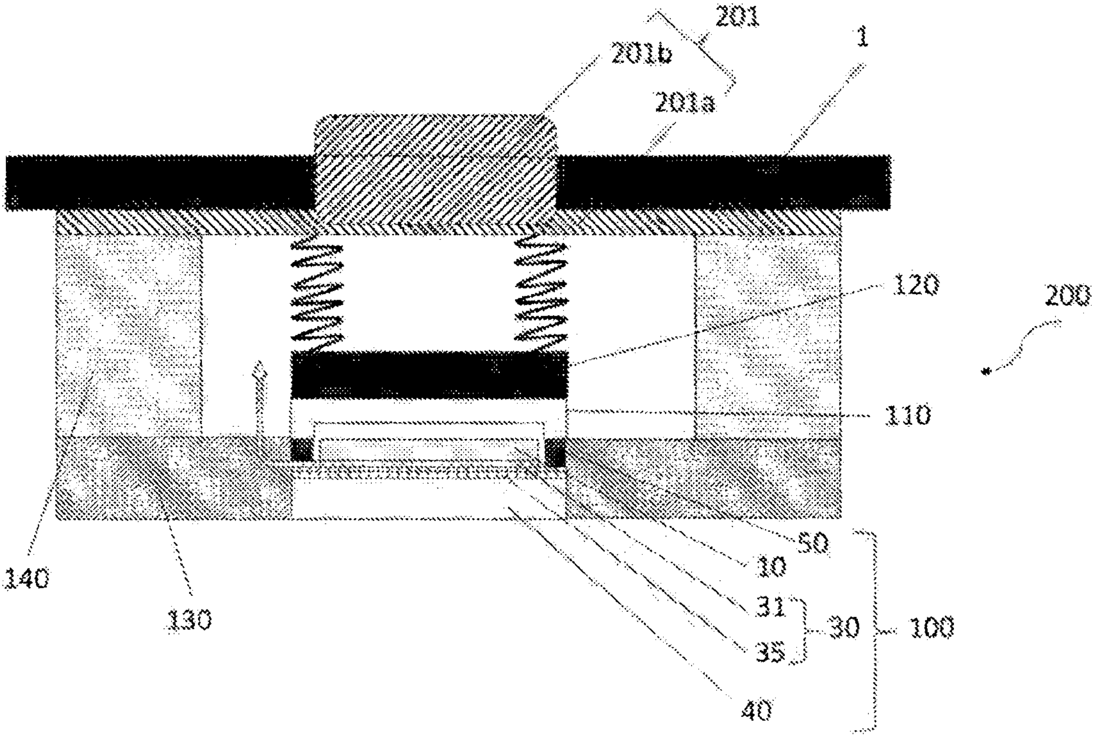
FIG. 6B illustrates a device according to the present disclosure, associated with a vehicle safety apparatus.

The device 200 according to the present disclosure may have a generally circular, square, rectangular or polygonal shape, in the main plane (x, y). As shown in FIG. 6B, it is intended to be arranged between the safety apparatus 1 and the individual seated in the vehicle. The face of the device 200, located on the side of the support layer 30 of the vibration sensor 100 (and on the side of the impedance matching layer 40 when the latter is present), is placed against the thorax of the individual, preferentially in an area where the heart beats or the respiratory rate are palpable. The other face of the device 200, located on the side of the acoustic attenuation member 110 (and the mechanical attenuation member 120, if present), is held against the safety apparatus 1. The contact between the device 200 and the apparatus 1 is preferentially carried out by means of a sliding fastener 201 (FIG. 6B): in particular, the face of the device 200 is rigidly connected (adhesively bonded or mechanically attached) to a support element 201*a* of the coupler 201, which element is attached to the safety apparatus 1 by a sliding clip 201*b*.

The device 200 according to the present disclosure has the advantage of greatly attenuating the frequencies outside the range of frequencies to be measured (range of frequencies typically between 0.2 Hz and 500 Hz for heart rates and respiratory rhythms, or even frequencies less than or equal to 70 Hz) and also to attenuate parasitic frequencies located within the frequency range of interest. It has been observed, in particular, that speech and other ambient sounds do not contaminate the measured signal. The sound environment of the individual at the time the measurement is taken therefore does not need to be calm and silent. This is possible owing to the particular structure of the vibration sensor 100 as well as due to the presence of the acoustic attenuation member 110.

In addition, the presence of the mechanical attenuation member 120 (or as will be described below with reference to the safety system, subject matter of the present disclosure, the presence of at least one mechanical energy absorber 210) significantly attenuates the mechanical vibrations produced by the motor in operation and optionally the irregularities of the road, vibrations that are transmitted to the safety apparatus 1 via the chassis of the vehicle. Neutralizing these parasitic mechanical vibrations allows a reliable and reproducible capture of the vital signals of the individual by the vibration sensor 100.

Advantageously, the device 200 is associated with a fabric 130 and a foam 140 to improve user comfort (FIG. 6B). The fabric 130 may border, for example, the support layer 30 and the impedance matching layer 40 if it is present; it may generally border all or part of the vibration sensor 100 and thus provide a smooth and uniform contact surface with the individual, which will make it possible to accommodate the user morphologies, the types of clothing and/or the adjustment variations of the safety apparatus 1. The foam 140 typically forms the link between the fabric 130 and the fastener 201; it is flexible and deformable and does not modify or only very slightly modifies the mechanical filter defined by the mechanical attenuation member 120.

The fabric 130 may be formed from cotton, nylon, or even polyethylene; the foam 140 may be formed from polyurethane, polyethylene or polystyrene.

The device 200, associated with a safety apparatus 1 in a vehicle, allows the measurement of at least one raw signal representative of a periodic vital signal of the individual installed in the vehicle.

Figures 5A, 5B, 5C:
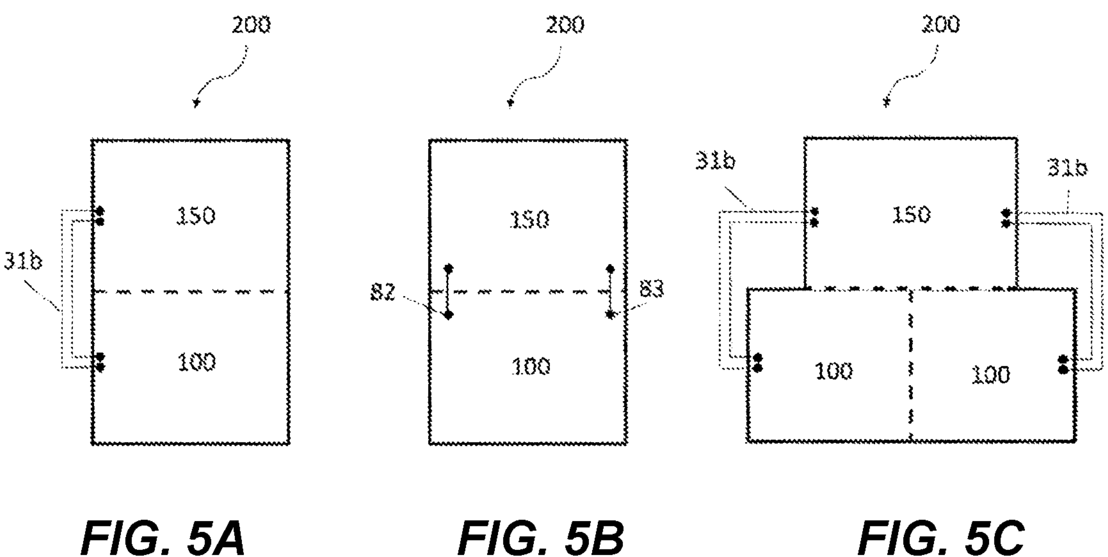
FIGS. 5A-5C show various configurations of devices for measuring a periodic vital signal, according to the present disclosure.

To analyze and interpret the raw signal and then extract the periodic vital signal or information relating to this vital signal, the device 200 further comprises an electronic terminal 150 electrically connected to the vibration sensor 100. It should be noted that the device 200 may comprise a vibration sensor 100 (FIGS. 5A and 5B) or a plurality (two, or even more) of sensors 100 connected to the electronic terminal 150 (FIG. 5C). When there are several sensors 100, it is possible to measure the same signal or different vital signals (heart rate and breathing) of the individual.

To connect the vibration sensor 100 and the electronic terminal 150, the printed circuit 31 of the vibration sensor 100 may comprise a wire connection element 31*b*, for example, a strip in the form of a web as shown in FIGS. 2A, 2B, 3A, 3B and 5A. The end piece of the wire connection element 31*b* comprises electrical contact connectors, connected to the electrical terminals 32, 33 of the printed circuit 31, which can be connected to the electronic terminal 150.

The electronic terminal 150 can be attached to the sensor 100 or located spaced apart from the sensor 100, in particular, on an attachment module for attachment to the safety apparatus 1 or to another part of the vehicle. The electronic terminal 150 can be connected or integrated to a more complex external system, such as a monitor that is fixed or optionally transportable.

Alternatively, the electronic terminal 150 can be arranged on the acoustic attenuation member 110 and can form all or part of the body 120*a* of the mechanical attenuation member 120. This configuration ensures great compactness of the device 200. In this case, it is possible to envisage a wire connection element 31*b* for electrically connecting the vibration sensor 100 and the terminal 150, but contact plugs 82, 83 rising vertically from the printed circuit 31 of the sensor 100 to the surface of the acoustic attenuation member 110, via the stiffening structure 50, for example (FIG. 5B).

The terminal 150 can comprise various electronic stages enabling it to analyze and interpret the raw signal measured by the vibration sensor 100. An analog stage for conditioning the raw signal measured by the vibration sensor 100 will first amplify and filter the electrical signal received from the sensor 100. This stage is typically composed of a first block of the charge amplification type whose resistance ratio sets the amplification gain of the electrical signal received from the sensor 100, and a second block of the Sallen & Key filter type making it possible to filter the frequencies beyond the acoustic spectrum of the targeted vital signals. The electronic terminal 150 then comprises a stage of analog to digital conversion of the signal coming from the conditioning stage. Then, a processing stage of the digital signal, composed of a microcontroller, performs the shaping of the signal by calculating a Shannon energy envelope function. Finally, from the shaped signal, the output parameter of interest, representative of the vital signal, can be calculated.

The collected data, relating to the vital signal or the output parameter of interest, can be interpreted in real time and trigger the response of a secondary system that is comprised in the device 200 or is external. The response can be an information feedback (visual, acoustic, mechanical, vibratory, etc.) and/or the triggering of one or more actions, for example:

mechanical(s): opening/closing of a system, electrical(s): turning on/turning off/varying a system, hydraulic, pneumatic, thermal, etc.

In all cases, the response of the secondary system aims to inform the individual (typically the driver of the vehicle), or to alert him or her, if the detected vital signal reveals that there is a risk of falling asleep or other abnormal situation.

To authorize the transmission of the output parameter of interest to a possible external system, the electronic terminal 150 may comprise a communication stage. Known connection protocols (CAN, UART, USB) or wireless data transmission, (Wi-Fi, BLUETOOTH®, etc.) may be used, for example.

In order to make the device 200 autonomous, it is also possible to provide a battery, preferentially rechargeable, allowing energy to be supplied to the aforementioned vibration sensor 100 and/or different stages of the electronic terminal 150. If the terminal 150 is remote to an area of the dashboard of the vehicle, it will be able to be powered by the battery of the vehicle.

As mentioned above, the device 200 can be broken down into various configurations:

a portable and autonomous device, capable of being positioned on any vehicle safety apparatus 1;

a fixed device, wherein the terminal 150 is connected to the sensor 100 by wire or integrated into a fixed and more complex external system (system attached to the dashboard of the vehicle or integrated with the dashboard).

The present disclosure also relates to a safety system for a vehicle comprising a safety apparatus 1 rigidly connected (directly or indirectly) with the chassis of the vehicle, at least at one contact point 2 (FIG. 1). The safety apparatus 1 can be directly connected to the chassis, usually via at least three contact points 2, for example, for a seatbelt. Alternatively, the safety apparatus 1 can be indirectly connected to the chassis, when the apparatus 1 is rigidly connected to the seat 3 of the vehicle, which seat is rigidly connected with the chassis, in one or more contact points 2.

The safety system comprises the aforementioned device 200 for measuring at least one periodic vital signal of an individual (for example, the driver of the vehicle), attached to the safety apparatus 1 by a sliding fastener 201.

When it is provided with the mechanical attenuation member 120, the device 200 allows the collection and efficient analysis of a vital signal of the individual in the vehicle in operation because it insulates the vibration sensor 100 from the mechanical vibrations of the engine transmitted to the safety apparatus 1 by the chassis, as will be shown below in the example of application.

A device 200 according to the present disclosure, without the mechanical attenuation member 120, can also be implemented in the safety system. In this case, the safety system comprises at least one mechanical energy absorber 210 placed at least at one contact point 2, so as to insulate the safety apparatus 1 from the vibrations of the chassis, upstream of the vibration sensor 100.

In the case where the safety apparatus 1 is connected to the chassis in three (or optionally four) contact points 2, it is advantageous to position a mechanical energy absorber 210 at least at one contact point 2, or even at each of the contact points 2. In the case where the safety apparatus 1 is connected to the seat 3, a mechanical energy absorber 210 is preferentially positioned at the contact point(s) 2 between the seat 3 and the chassis of the vehicle.

Of course, it is also possible to position a mechanical energy absorber 210 at the contact point(s) 2 between the seat 3 and the chassis, in the case where the safety apparatus 1 is connected directly to the chassis.

The mechanical energy absorber 210 will form a mechanical filter and therefore comprises a body (mass) and a damper (stiffness, coefficient of friction), as has been described with reference to the mechanical attenuation member 120.

Finally, it is conceivable to implement both the device 200 provided with a mechanical attenuation member 120 and the mechanical energy absorbers 210 offset over all or part of the direct or indirect contact points 2 between the safety apparatus 1 and the chassis. Such a configuration allows further improvement of the quality of the raw signal measured by the vibration sensor 100, by drastically limiting the parasitic noises and vibrations related to the operation of the engine and to the movement of the vehicle.

EXAMPLE EMBODIMENT

An example of manufacturing the vibration sensor 100 and the device 200 will now be described. Of course, this example is not limiting because there are other methods for stacking and assembling different types of layers, capable of being implemented to produce the device 200, according to the present disclosure.

In order to manufacture the stack of layers 10 of the vibration sensor 100, it is, in particular, possible to use a transfer method close to that described by T Dufay et al. in the publication "Flexible PZT thin film transferred on polymer substrate" (Surface and Coatings Technology, Elsevier, 2018, 343, pp. 148-152).

A solution of PZT precursor is deposited by spin-coating on a sacrificial substrate (for example, aluminum), to form a viscous layer. An opening is made through the layer in order to allow the passage of an electrical path. Then, a heat treatment at 650° C. is applied to crystallize the PZT and form an active layer 11 made of piezoelectric material with a thickness of 5 microns.

A platinum contact electrode 12, of 400 nm thickness, is deposited by a chemical vapor deposition technique (for example, PECVD) on the upper (free) face of the active layer 11 made of PZT, then covered with a polyurethane adhesive layer. An opening is also made through the electrode/adhesive layer stack for the passage of the electrical path. A temporary layer made of polymer (for example, PET), 200 microns thick, is attached to the thermal compression polyurethane adhesive layer, to facilitate the handling of the active layer 11. The temporary layer is open to allow the passage of the electrical path, and filled with conductive glue, which will form the conductive via 14, in electrical contact with the contact electrode 12. The sacrificial substrate is then chemically etched until the lower face of the active layer 11 made of PZT is bare. The other contact electrode 13 and the stud 12*a*, in electrical contact with the via 14, are formed by aluminum deposition (about 400 nm) on the lower face of the PZT.

This manufacturing method can allow the creation of a PZT film having large lateral dimensions, which are then cut to define the active layer 11 with the lateral dimensions desired for its integration into the vibration sensor 100 according to the present disclosure. In the example described, the active layer 11 has lateral dimensions (along the main plane (x, y)) of 5 mm by 15 mm.

A printed circuit board (PCB) 31 is then chosen having a thickness of 100 microns, lateral dimensions substantially identical to those of the active layer 11 and comprising two electrical terminals 32, 33. An anisotropic conductive film (ACF) 20 is laminated on the printed circuit 31. Using a handling machine (of the "Pick and Place" type), the active layer 11 is positioned opposite the connection layer 20, so that each electrode 12*a*, 13 (on the lower face of the active layer 11) is in line with an electrical terminal 32, 33 of the printed circuit 31; then an assembly by thermocompression is carried out.

The temporary polymer layer can then be removed.

The printed circuit 31 is then bonded to a PVC membrane 35, with a thickness of 300 microns and lateral dimensions (or diameter) 50 mm, to finalize the formation of the support layer 30. An impedance matching layer 40 made of silicone, of thickness 3 mm, can be assembled by lamination, screen printing or molding against the membrane 35. A polypropylene stiffening structure 50 and a silicone peripheral seal 60 are attached to the periphery of the membrane 35 by fitting.

A silicone cover, forming the acoustic attenuation member 110 above and at a distance from the active layer 11, is molded, then glued onto the stiffening structure 50. It has a thickness of 2 mm.

A mechanical attenuation member 120 can also be formed: it is composed of rubber pillars 120*b*, bonded to a steel body 120*a* of thickness 5 mm. The body 120*a* is glued against the acoustic attenuation member 110. On the side of their free end, the pillars 120*b* are glued to the support element 201*a* of a fastener 201, which can be associated with the safety apparatus 1 of a vehicle (a seatbelt 1 in this example). The fastener 201 may be formed, for example, from polyoxymethylene.

For user comfort, the assembly can be covered with a fabric 130 and/or a foam 140, at the periphery of the measurement area.

In this example, the printed circuit 31 comprises a wire connection element 31*b* (web) that makes it possible to connect the electrical terminals 32, 33 of the printed circuit 31 to the electronic terminal 150, via electrical contact plugs. The terminal 150 comprises the electronic stages set out in the general description. It is, for example, placed under the seat 3 of the user.

Figures 7A, 7B:
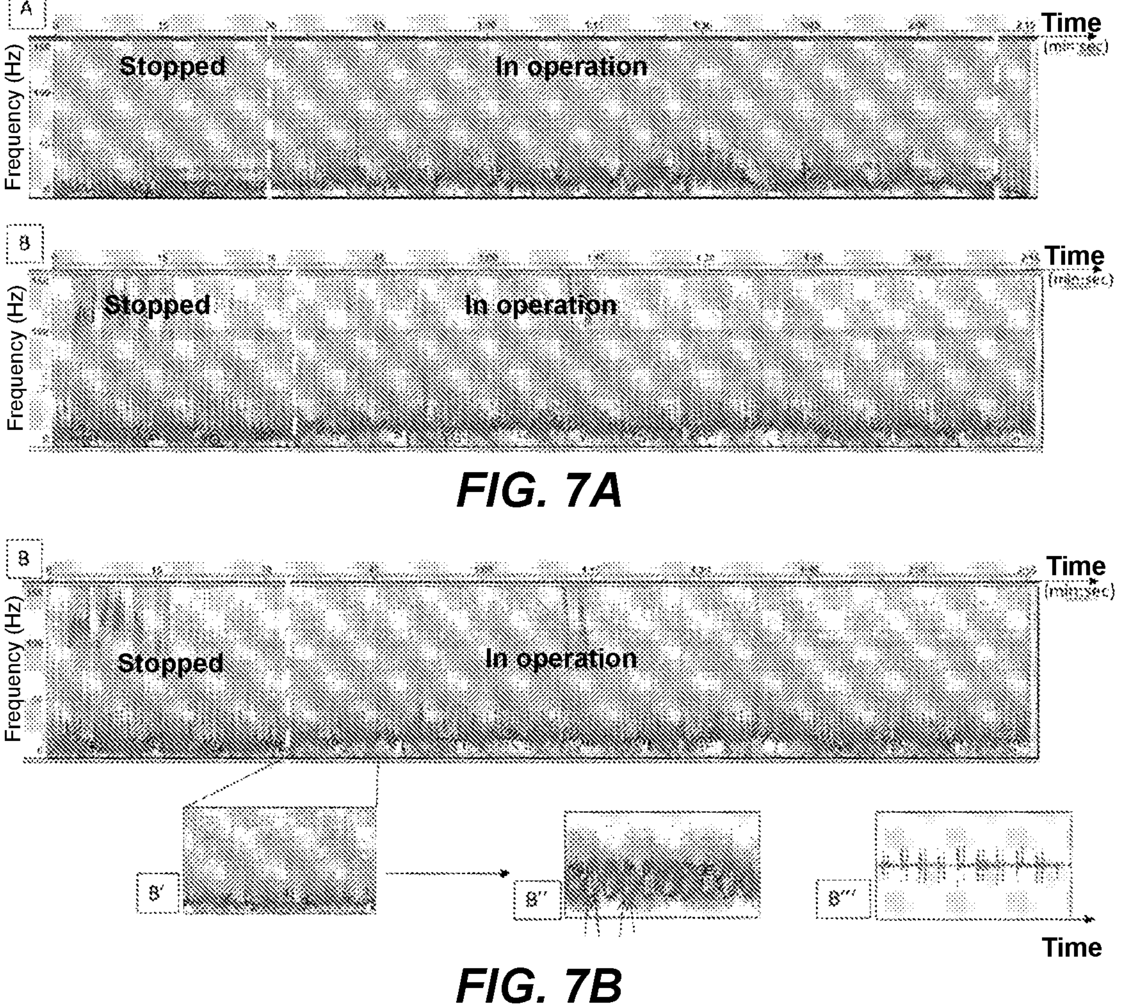
FIG. 7A shows a spectrogram A measured by a vibration sensor (alone) as included in the device according to the present disclosure and a spectrogram B measured by a device according to the present disclosure.
FIG. 7B shows the spectrogram B, a spectrogram B' extracted from the spectrogram B, a spectrogram B" after applying a frequency filter, and a vital signal B''' as a waveform, captured and processed by a device according to the present disclosure.

With the device 200 thus formed, an example of application to the measurement of the heart rate of a driver is shown in FIGS. 7A and 7B. To measure the heart rate, the device 200 is adjusted in height along the seatbelt 1, so as to be arranged on the thorax of the individual, substantially on the left, the impedance matching layer 40 of the vibration sensor 100 being placed in contact with the clothing, and the mechanical attenuation member 120 being in contact with the seatbelt 1 via the sliding clip 201.

FIG. 7A shows two raw spectrograms A, B, acquired on a frequency scale ranging from 0 to 150 Hz, by a vibration sensor 100 as previously described (acquisition frequency 128 kHz). In the case of spectrogram A, the measuring device comprises neither the acoustic attenuation member 110 nor the mechanical attenuation member 120; the safety system also does not comprise a mechanical energy absorber 210. In the case of spectrogram B, the device 200 according to the example described above comprises an acoustic attenuation member 110 and a mechanical attenuation member 120.

When the vehicle is stopped, both spectrograms A, B show regular peaks, which, after processing, provide reliable information on the heart rate of the driver; this information is reliable regardless of the surrounding sound level in the vehicle. Conversely, as soon as the vehicle is in operation, the vibrations of the engine generate tremendous parasitic noise and vibrations, which make spectrogram A unusable. The device 200 according to the present disclosure makes it possible to obtain a much less noisy spectrogram B, owing to the presence of the acoustic and mechanical attenuation members 110 and 120. It should be noted that a similar result could be obtained with a device 200 without the mechanical attenuation member 120, in the case where the vehicle safety system comprises at least one mechanical energy absorber 210, at the direct or indirect contact point(s) 2 between the seatbelt 1 and the chassis.

FIG. 7B shows an extract B' of about 15 s of spectrogram B, within the period during which the vehicle is in operation. The regular peaks representative of the heart rate of the driver are more clearly distinguished.

Spectrogram B" is obtained by applying a filter between 40 Hz and 70 Hz and normalizing the signal. The peaks indicated on the spectrogram B" can be visualized in the form of a wave: This is the signal B"', which reveals the peaks representative of the heart rate of the driver. Thus, from the signal B"', it is possible to extract the periodic signal and/or an output parameter, representative of the heart rate of the individual, with an excellent level of precision.

It is therefore possible to reliably detect a change in the heart rate (or similarly, of the respiratory rate) likely to announce that the driver is falling asleep or other risky situation. In such a case, the device 200 is able to trigger an action (sound or light signal, for example) as mentioned above.

As has just been shown and generally, the non-intrusive device 200 for measuring a periodic vital signal according to the present disclosure provides reliable information regarding the vital signal of the driver, regardless of the sound environment in the vehicle, when stopped or in operation.

Of course, the present disclosure is not limited to the described embodiments and examples, and variant embodiments can be provided thereto without departing from the scope of the invention as defined by the claims.

The invention claimed is:

1. A device for measuring at least one periodic vital signal from an individual, intended to be attached to a safety apparatus of a vehicle so as to be arranged between the individual and the apparatus, the device comprising:

a vibration sensor comprising:

a stack of layers extending parallel to a main plane and including an active layer of piezoelectric material and two contact electrodes arranged on at least one face of the active layer;

a flexible support layer configured to transmit a deformation to the active layer of the stack of layers, at each pulse of the vital signal, the support layer extending parallel to the main plane and including a printed circuit comprising two electrical terminals, the support layer configured to be arranged against the individual; and an electrical connection layer arranged between the stack of layers and the support layer, the electrical connection layer connecting each contact electrode to an electrical terminal;

an acoustic attenuation member configured to be arranged between the safety apparatus and the vibration sensor, the acoustic attenuation member being rigidly connected to the support layer and arranged above and spaced apart from the stack of; and an electronic terminal connected to the vibration sensor to analyze and interpret a raw signal and extract the periodic vital signal or an output parameter representative of the periodic vital signal.

2. The device of claim 1, wherein the acoustic attenuation member comprises a cover composed of a flexible material having a hardness of between 10 Shore 00 and 80 Shore 00, and rigidly connected to the support layer by a periphery of the cover.

3. The device of claim 2, wherein the cover is heterogeneous and comprises a second rigid material, the second rigid material comprising a metal or a polymer having a hardness of between 10 Shore D and 80 Shore D.

4. The device of claim 1, further comprising a mechanical attenuation member on or integrated in whole or in part in the acoustic attenuation member, the mechanical attenuation member configured to be in direct or indirect contact with the safety apparatus.

5. The device of claim 4, wherein the mechanical attenuation member comprises at least one damper.

6. The device of claim 1, wherein the active layer of the stack of layers has a thickness of less than or equal to 20 microns and a Young's modulus greater than or equal to 60 GPa.

7. The device of claim 1, further comprising an impedance matching layer having an acoustic impedance between $5 \cdot 10^5$ Pa*s/m and $3 \cdot 10^6$ Pa*s/m, and arranged on a face of the support layer opposite a face of the support layer in contact with the electrical connection layer.

8. The device of claim 7, wherein:

the contact electrodes have a cumulative thickness of less than twice the thickness of the active layer;

the support layer is self-supporting and has a thickness of less than or equal to 500 microns; and the impedance matching layer has a thickness greater than or equal to 10 microns.

9. The device of claim 8, wherein the support layer includes a membrane arranged on a face of the printed circuit opposite a face of the printed circuit in contact with the electrical connection layer.

10. The device of claim 1, wherein the support layer comprises a stiffening structure rigidly connected to a peripheral zone of the support layer, the acoustic attenuation member being rigidly connected to the stiffening structure.

11. The device of claim 1, wherein the electronic terminal comprises:

an analog stage for conditioning a raw signal measured by the vibration sensor;

an analog to digital conversion stage of the signal coming from the conditioning stage; and a digital signal processing stage for shaping the digital signal and calculating an output parameter representative of the vital signal.

12. A vehicle safety system, comprising:

a safety apparatus associated with a seat and rigidly connected to a chassis of the vehicle at least at one direct or indirect contact point;

a device according to claim 1 for measuring at least one periodic vital signal of an individual, the device attached to the safety apparatus by a sliding fastener; and at least one mechanical energy absorber placed at least at one contact point so as to insulate the safety apparatus from mechanical vibrations of the chassis.

13. The vehicle safety system of claim 12, wherein the safety apparatus is directly connected to the chassis by at least three contact points, and further comprising a mechanical energy absorber integrated into at least one of the at least three contact points.

14. The vehicle safety system of claim 12, wherein the safety apparatus is connected to the seat, is the seat being rigidly connected to the chassis by at least one contact point, and further comprising a mechanical energy absorber integrated into said the at least one contact point.

15. The device of claim 5, wherein the mechanical attenuation member further comprises a body forming a mass.

16. The device of claim 3, further comprising a mechanical attenuation member on or integrated in whole or in part in the acoustic attenuation member, the mechanical attenuation member configured to be in direct or indirect contact with the safety apparatus.

17. The device of claim 16, wherein the mechanical attenuation member comprises at least one damper.

18. The device of claim 17, wherein the active layer of the stack of layers has a thickness of less than or equal to 20 microns and a Young's modulus greater than or equal to 60 GPa.

19. The device of claim 18, further comprising an impedance matching layer having an acoustic impedance between $5 \cdot 10^5$ Pa*s/m and $3 \cdot 10^6$ Pa*s/m, and arranged on a face of the support layer opposite a face of the support layer in contact with the electrical connection layer.

* * * * *